United States Patent [19]

Watson

[11] Patent Number: 5,032,613

[45] Date of Patent: Jul. 16, 1991

[54] METHOD AND COMPOSITION FOR TREATING ARTHRITIS

[75] Inventor: W. Keith R. Watson, 2749 Via Viejas, Alpine, Calif. 92001

[73] Assignees: W. Keith R. Watson; William W. Haefliger, both of Pasadena, Calif.; a part interest

Related U.S. Application Data

[63] Continuation of Ser. No. 828,941, Feb. 12, 1986, Pat. No. 4,898,884.

[21] Appl. No.: 467,278

[22] Filed: Feb. 5, 1990

[51] Int. Cl.$^5$ .................. A61K 31/10; A61K 31/19; A61K 31/185

[52] U.S. Cl. .................. 514/553; 514/557; 514/708; 514/936

[58] Field of Search ............... 514/553, 557, 708, 936

Primary Examiner—Stanley J. Friedman
Attorney, Agent, or Firm—William W. Haefliger

[57] ABSTRACT

A solution of DMSO and a body reactive agent (such as citric acid) is provided, and is typically topically applied to the body.

7 Claims, 1 Drawing Sheet

METHOD AND COMPOSITION FOR TREATING ARTHRITIS

This application is a continuation of Ser. No. 828,941, filed Feb. 12, 1986, now U.S. Pat. No. 4,898,884.

BACKGROUND OF THE INVENTION

This invention relates generally to remedial treatments for arthritis, to relieve pain and/or reduce inflammation and deformation or the causes thereof. More particularly, it concerns a composition and method for removing arthritic calcareous deposits.

There exists a long recognized need for techniques or processes which will alleviate arthritic pain and swelling. None of the current remedies, such as the use of pain killers, serves to reduce arthritic calcareous deposits, and reduce or eliminate inflammation without requiring surgery.

SUMMARY OF THE INVENTION

It is a major object of the invention to provide method and composition that will meet the above need. Basically, the method of treating an arthritic zone underlying a skin area, in accordance with the invention, includes the steps:

a) providing a non-toxic solution that consists essentially of citric acid or other chelate dissolved in DMSO, b) and topically applying said solution to the skin area overlying the arthritic zone.

It is found that the solution penetrates the skin and serves to alleviate symptoms of arthritics, such as inflammation, pain and swelling. As will appear, the solution may be applied to a porous pad, to wet same, and the wetted pad may be topically applied at regular intervals to the skin, as at night for as long as necessary to obtain the relief. Several days and in some cases several weeks are required, depending upon the severity of the disease, the skin area being kept wetted by the solution, and wetted pads being replaced at intervals for this purpose. Other body reactive agents are usable.

Other objects of the invention include providing for carriage of the solution as in a porous pad applicable to the skin, and packaging of the wetted pad.

These and other objects and advantages of the invention, as well as the details of an illustrative embodiment, will be more fully understood from the following discussion and drawings, in which:

DRAWING DESCRIPTION

DETAILED DESCRIPTION

Figure 1:
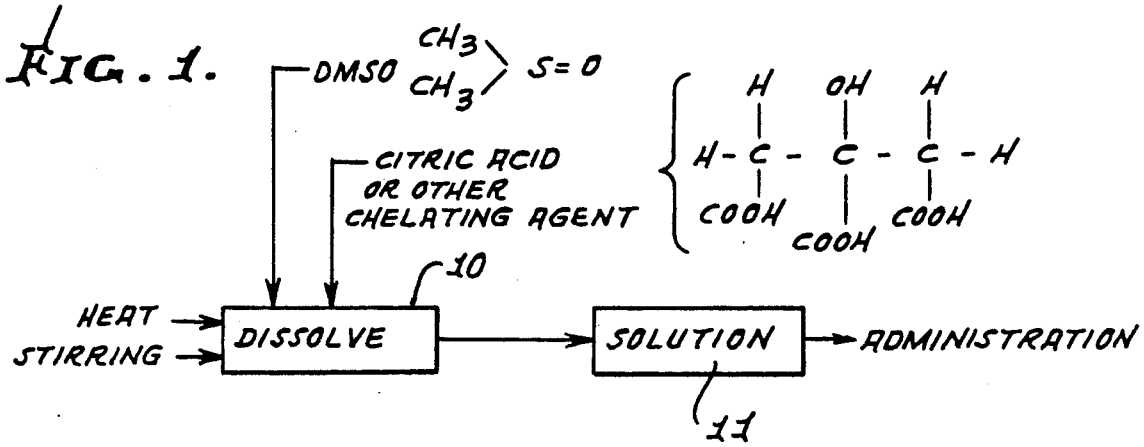
FIG. 1 is a flow diagram.

Referring first to FIG. 1, 10 indicates a mixing step involving mixing of DMSO (dimethyl sulfoxide) with citric acid to produce a solution at 11. Typically, the pure citric acid is in sold crystalline form and is dissolved in the DMSO, in liquid state. Specifically, 20 to 50 weight percent citric acid is dissolved in 80 to 50 weight percent DMSO, under heating (as by microwave oven at about 140°–200° F.) and agitation (as by stirring) for about 45 to 80 seconds, to produce the solution, which is preferably anhydrous. Citric acid monohydrate is usable for this purpose, in the same proportions.

Figure 2:
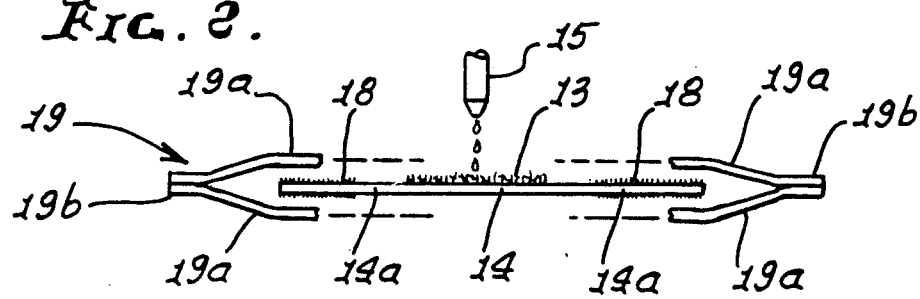
FIG. 2 is a side elevation showing solution wetting of a carrier.
Figure 4:
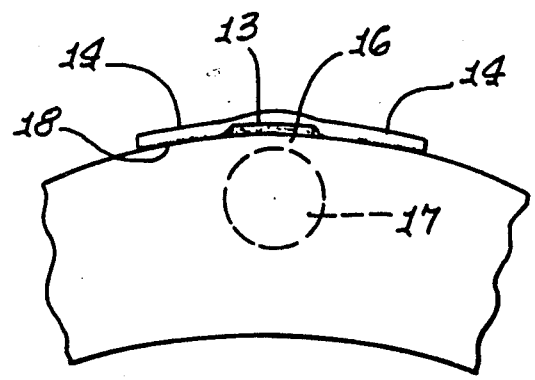
FIG. 4 is an elevation showing application of the wetted carrier to a skin area overlying an arthritic zone.

FIG. 2 shows the provision of a porous mechanical carrier for the solution, and application of the solution to the carrier to wet same. For example, the carrier may take the form of a gauze pad 13 on a band 14 with adhesive 18 on band extends 14a for attaching the band to a user's (human or animal) anatomy. The solution may be applied as by droplets from a syringe 15, to saturate the pad. FIG. 4 shows the pad 13 typically applied to the skin area 16 overlying the arthritic zone 17, such as a bone or joint. The pad is held in position by the band adhesive areas 18 adherent to the skin. A BAND-AID may serve this purpose.

Figure 3:
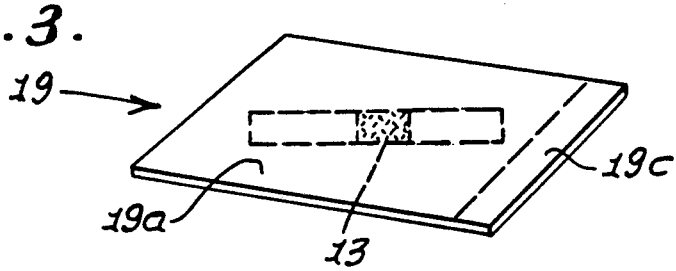
FIG. 3 is a perspective view showing a package for the FIG. 2 carrier.

FIGS. 2 and 3 also show the enclosure of the saturated pad and band in a package 19, as for example aluminum foil, with upper and lower layers 19a edge joined at 19b. This maintains the saturated pad in hermetically sealed condition, for shipment, to prevent moisture contact with the pad prior to use. See also tear strip 19c.

In use, the acid-DMSO complex solution penetrates the skin, sub-cutaneously, and contacts the arthritic area, characterized by formation of arthritic bone or joint tissue containing calcium phosphate. The citric acid contacts that tissue and reacts therewith to form calcium citrate carried away in the blood stream and removed by liver and kidney function.

The reaction is believed to proceed typically as follows: citric acid plus calcium phosphate (calcareous deposit)

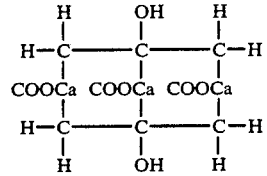

Other reaction products can include "one" calcium citrate, and "two" calcium citrate, expressed as follows:

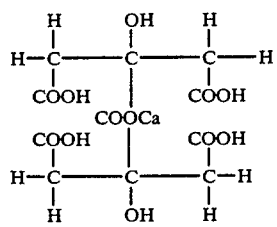

and,

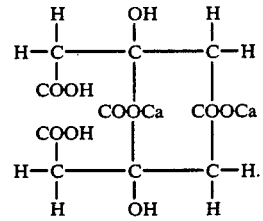

These reaction products are soluble in body fluid such as blood. The treatment is repeated (pad applied) as long as necessary (as at regular intervals, such as during the night) to obtain relief from pain, to reduce or eliminate inflammation, and to reduce swelling and calcareous deposits.

Chelating agents other than citric acid may be employed, and in the same manner as described above for citric acid. Such agents included E.D.T.A. (ethylenedinitrilo) tatraacetic acid, which complexes heavy metals including calcium, and L-tartaric or M-tartaric acid which reacts with calcium deposits to form calcium tartrate.

The porous mechanical carrier as described may be used to carry other solutions consisting essentially of a body reactive agent dissolved in DMSO; thus, the described technique is usable to replace hypodermic injections, the advantage being that the agent is carried into the bloodstream without requiring skin puncturing. Also, slow administration is achieved. Examples of such agents include insulin, anaesthetics employed as during surgery, acetasalycilic acid (aspirin), procaine and other low molecular weight agents.

We claim:

1. A method of treating an arthritic zone underlying a skin area of a person or animal to be treated, which comprises
   topically applying to the skin area overlying the arthritic zone an effective amount of a solution that consists essentially of citric acid or citric acid monohydrate dissolved in DMSO, said solution consisting essentially of 20 to 50 weight percent citric acid, or citric acid monohydrate, and 80 to 50 weight percent DMSO.

2. The method of claim 1 including repeating a topical application of the solution at regular intervals.

3. The method of claim 1 wherein
   said solution is applied to an inflamed, painful and swollen skin area of the patient for a period of time and in an amount sufficient to alleviate said inflammation, pain and swelling.

4. A method of administering to the arthritic zone of a body reactive chelating agent to a person being treated, which comprises
   topically applying to the skin of said person an effective amount of a solution that consists essentially of said agent dissolved in DMSO, said agent selected from the group consisting of citric acid, L-tartaric acid, M-tartaric acid, and E.D.T.A.

5. The method of claim 4 wherein said agent is applied proximate an arthritic zone.

6. A solution composition for use in treating an arthritic zone underlying a skin area of a person or animal to be treated, that consists essentially of 20 to 50 weight percent citric acid dissolved in 80 to 50 percent DMSO in the presence of heat.

7. The composition of claim 6 wherein said solution composition is anhydrous.

* * * * *